(12) United States Patent
Westerhoff et al.

(10) Patent No.: US 10,823,649 B2
(45) Date of Patent: Nov. 3, 2020

(54) MICROFLUIDIC SEPARATION FROM WATER AND DIRECT OPTICAL DETECTION OF CHLORINE

(71) Applicants: Paul K. Westerhoff, Scottsdale, AZ (US); Shahnawaz Sinha, Chandler, AZ (US); Treavor Boyer, Scottsdale, AZ (US)

(72) Inventors: Paul K. Westerhoff, Scottsdale, AZ (US); Shahnawaz Sinha, Chandler, AZ (US); Treavor Boyer, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 98 days.

(21) Appl. No.: 16/146,160

(22) Filed: Sep. 28, 2018

(65) Prior Publication Data

US 2019/0094118 A1    Mar. 28, 2019

Related U.S. Application Data

(60) Provisional application No. 62/564,366, filed on Sep. 28, 2017.

(51) Int. Cl.
*G01N 1/40*        (2006.01)
*B01D 19/00*       (2006.01)
(Continued)

(52) U.S. Cl.
CPC ....... *G01N 1/4005* (2013.01); *B01D 19/0031* (2013.01); *B01L 3/502715* (2013.01);
(Continued)

(58) Field of Classification Search
CPC .... G01N 1/4005; G01N 21/05; G01N 21/255; G01N 21/3103; G01N 33/18; G01N 1/10;
(Continued)

(56) References Cited

U.S. PATENT DOCUMENTS

| 4,270,925 A * | 6/1981 | Isa | G01N 30/06 |
| | | | 422/62 |
| 2013/0061748 A1 * | 3/2013 | Sims | B01D 71/34 |
| | | | 95/46 |

(Continued)

*Primary Examiner* — Jamil Ahmed
(74) *Attorney, Agent, or Firm* — Fish & Richardson P.C.

(57) ABSTRACT

A microfluidic device includes a sample inlet for a fluid sample, a degassing chamber having a gas-permeable membrane and defining first and second portions separated by the gas permeable membrane, and a detection chamber. The sample inlet and the detection chamber are fluidly coupled to the first and second portions, respectively of the degassing chamber. The detection chamber is operably coupled to a light source and a detector. Assessing a concentration of chlorine gas in an aqueous sample includes providing an aqueous sample to a microfluidic device, separating gas from the aqueous sample in the microfluidic device, providing the gas to a detector, assessing the absorbance of the gas sample at a known absorption wavelength of chlorine, and based on the assessed absorbance of the gas sample at the known absorption wavelength of chlorine, assessing a concentration of chlorine gas in the aqueous sample.

20 Claims, 1 Drawing Sheet

(51) Int. Cl.
*G01N 21/25* (2006.01)
*G01N 21/31* (2006.01)
*G01J 3/00* (2006.01)
*G01N 33/18* (2006.01)
*G01N 21/05* (2006.01)
*B01L 3/00* (2006.01)
*G01N 1/22* (2006.01)
*G01N 21/03* (2006.01)
*G01N 1/10* (2006.01)

(52) U.S. Cl.
CPC ............ *G01J 3/00* (2013.01); *G01N 21/05* (2013.01); *G01N 21/255* (2013.01); *G01N 21/3103* (2013.01); *G01N 33/18* (2013.01); *B01L 2300/0654* (2013.01); *B01L 2300/0663* (2013.01); *B01L 2300/0816* (2013.01); *G01N 1/10* (2013.01); *G01N 21/31* (2013.01); *G01N 2001/2267* (2013.01); *G01N 2021/0346* (2013.01); *G01N 2021/054* (2013.01); *G01N 2201/08* (2013.01)

(58) Field of Classification Search
CPC ........... G01N 21/31; G01N 2001/2267; G01N 2021/0346; G01N 2021/054; G01N 2201/08; B01D 19/0031; B01L 3/502715; B01L 2300/0654; B01L 2300/0663; B01L 2300/0816; G01J 3/00
See application file for complete search history.

(56) References Cited

U.S. PATENT DOCUMENTS

| | | |
|---|---|---|
| 2016/0334311 A1 | 11/2016 | Westerhoff et al. |
| 2018/0095028 A1* | 4/2018 | Jourdainne ........ G01N 21/3504 |
| 2019/0056363 A1 | 2/2019 | Westerhoff et al. |
| 2019/0232230 A1* | 8/2019 | Richter ............. B01D 19/0068 |
| 2019/0391073 A1* | 12/2019 | Tanaka ..................... G01J 3/26 |

* cited by examiner

MICROFLUIDIC SEPARATION FROM WATER AND DIRECT OPTICAL DETECTION OF CHLORINE

CROSS-REFERENCE TO RELATED APPLICATION

This application claims the benefit of U.S. Application No. 62/564,366, filed on Sep. 28, 2017, which is incorporated by reference herein in its entirety.

STATEMENT OF GOVERNMENT INTEREST

This invention was made with government support under EEC-1449500 awarded by the National Science Foundation. The government has certain rights in the invention.

TECHNICAL FIELD

This invention relates to devices, systems, and methods for microfluidic separation of chlorine from water with direct optical chlorine detection in the gas phase.

BACKGROUND

Chlorine is one of the most widely used disinfectants in water treatment. It has played a significant role in the turn of the last century in doubling U.S. life expectancy by eliminating water borne diseases, such as cholera and typhoid. However, when in the presence of dissolved organic carbon in water, chlorine reacts to form harmful disinfection by-products (DBPs). Regulations in the U.S. include a requirement to measure and maintain detectable levels of chlorine disinfectant leaving water treatment plants and distribution systems. Currently, chlorine residual in the water (reported as $Cl_2$) is measured by various techniques, such as colorimetric reaction with specific reagents (e.g., dyes) plus spectrophotometric detection or electrochemical-based methods. Due at least in part to the cost, size, and complexity of the associated apparatus, as well as the additional costs associated with necessary reagents, the use of these techniques in the water industry remains limited despite the increasing occurrence of *Legionella* and other microbial water-borne pathogens in buildings with low or no chlorine residual.

SUMMARY

Microfluidic devices described herein detect and quantify gaseous chlorine in aqueous samples. These devices operate without added chemical reagents and are advantageously compact and robust. They require low sample volumes and are easy to transport and operate. Assessment of chlorine in the gas phase eliminates challenges associated with assessment of chlorine in the liquid phase, including interference from dissolved organic species and particles in water. Since the sensor is not in direct contact with the liquid, sensor fouling and associated sensor replacement and maintenance are reduced. These devices may be battery operated, and are suitable for detecting gaseous chlorine in water samples at sites that are difficult to access or have limited or no available power. Uses include routine monitoring of chlorine levels, as well as implementation in early warning schemes in water systems, buildings, pools and spas, treated wastewater effluent, reclaimed wastewater, and bottling industries.

In a first general aspect, a microfluidic device includes a sample inlet for a fluid sample, a degassing chamber, a light source, a detection chamber, and a detector. The degassing chamber includes a gas-permeable membrane and defines a first portion and a second portion separated by the gas permeable membrane. The sample inlet is fluidly coupled to the first portion of the degassing chamber, the detection chamber is fluidly coupled to the second portion of the degassing chamber, and the light source and the detector are operably coupled to the detection chamber.

Implementations of the first general aspect may include one or more of the following features.

The microfluidic device may include a gas inlet fluidly coupled to the first portion of the degassing chamber. In some cases, the light source includes a light-emitting diode. In certain cases, the detector includes a differential optical absorption spectrometer, a charge-coupled device detector array, or both. The microfluidic device may include a battery operatively coupled to the detector, a data acquisition system operably coupled to the detector, or both. A computing device may be operably coupled to the data acquisition system.

In a second general aspect, a microfluidic system includes a microfluidic device. The microfluidic device includes a sample inlet for a fluid sample, a degassing chamber including a gas-permeable membrane and defining a first portion and a second portion separated by the gas permeable membrane, and a detection chamber. The sample inlet is fluidly coupled to the first portion of the degassing chamber, and the detection chamber is fluidly coupled to the second portion of the degassing chamber.

Implementations of the second general aspect may include one or more of the following features.

The microfluidic system or the microfluidic device may include a light source operably coupled to the detection chamber. The light source may be a light-emitting diode. The microfluidic system or the microfluidic device may include a detector operably coupled to the detection chamber. The microfluidic system may include one or more additional microfluidic devices, each including an additional detection chamber, with the detector operably coupled to each additional detection chamber.

In a third general aspect, assessing a concentration of chlorine gas in an aqueous sample includes providing an aqueous sample to a microfluidic device, separating gas from the aqueous sample in the microfluidic device, providing the gas to a detector, assessing the absorbance of the gas sample at a known absorption wavelength of chlorine, and based on the assessed absorbance of the gas sample at the known absorption wavelength of chlorine, assessing a concentration of chlorine gas in the aqueous sample.

Implementations of the third general aspect may include one or more of the following features.

Separating the gas from the aqueous sample may include contacting the aqueous sample with a gas-permeable membrane, contacting a purge gas with the aqueous sample, or both. The aqueous sample may be provided to the microfluidic device continuously. The aqueous sample may be fluidly separated from the detector. Assessing the concentration of chlorine gas in the aqueous sample typically occurs without combining a chemical reagent with the aqueous sample.

DETAILED DESCRIPTION

Figure 1:
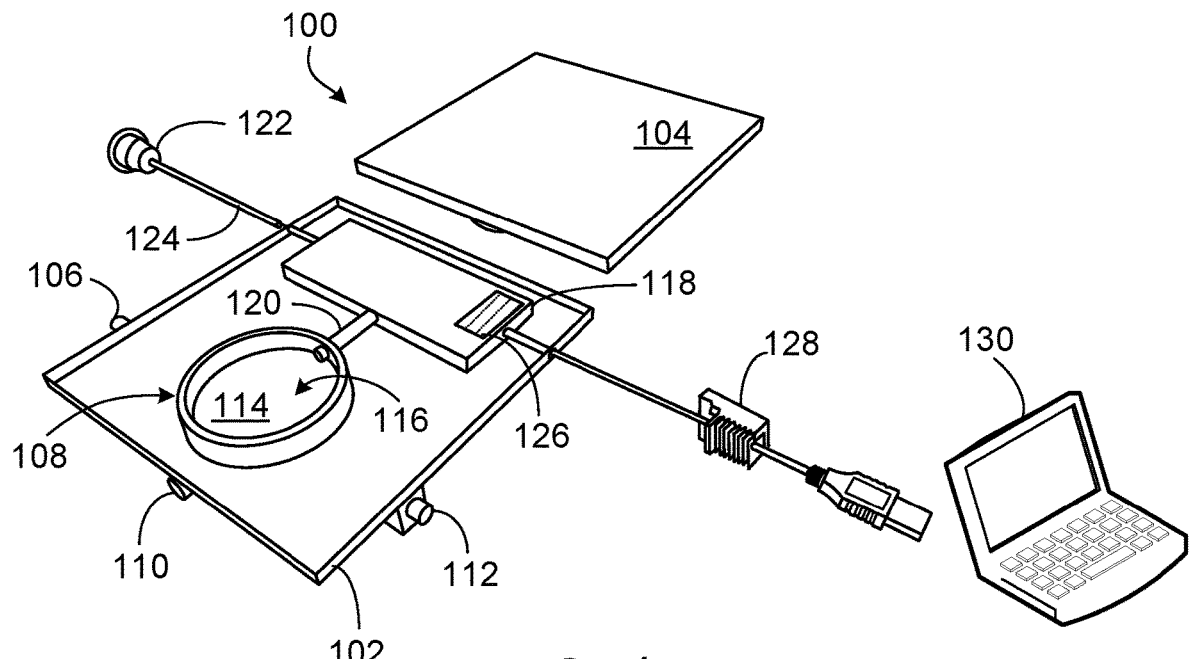
FIG. 1 is an exploded perspective top view a microfluidic device for quantifying gaseous chlorine in aqueous samples.

FIG. 1 is an exploded top view of microfluidic device 100 designed to quantify gaseous chlorine in an aqueous sample. Microfluidic device 100 includes base 102 and cover 104. Cover 104 may be sealed to base 102. Base 102 includes sample inlet 106, degassing chamber 108, gas inlet 110, and waste outlet 112. Sample inlet 106 is configured to provide an aqueous sample to degassing chamber 108, and gas inlet 110 is configured to provide a purge gas to degassing chamber 108. Waste outlet 112 is configured to allow egress of fluid from a fluid sample provided to microfluidic device 100. Degassing chamber 108 includes membrane 114. Membrane 114 is a gas-permeable membrane positioned between a lower portion of degassing chamber 108 and upper portion 116 of the degassing chamber. Examples of suitable gas permeable membranes (e.g., permeable to air or an inert gas such as nitrogen or helium) include nylon, polyethylene terephthalate (PET), and other suitable materials. Upper portion 116 of degassing chamber 108 is fluidly coupled to detection chamber 118 via conduit 120.

Light source 122 is operatively coupled to detection chamber 118 via conduit 124. In some embodiments, microfluidic device 100 includes light source 122. In certain embodiments, light source 122 is external to microfluidic device 100. Light source 122 is typically a light emitting diode (LED) that emits infrared (IR), ultraviolet (UV), or visible (VIS) light. In some embodiments, two or more light sources of the same or different wavelengths are operatively coupled to detection chamber 118. Conduit 124 is typically a fiber optic cable selected to couple light from light source 122 to detection chamber 118.

In some embodiments, detection chamber 118 includes detector 126. In certain embodiments, detector 126 is external to microfluidic device 100, and can be coupled to one or more microfluidic devices. Detector 126 includes a ruled optical grating, a differential optical absorption spectrometer (DOAS), and a charge-coupled device (CCD) detector array configured to detect UV, VIS, or IR light. The CCD detector array is operatively coupled to data acquisition system 128. Data acquisition system 128 may be operatively coupled to computing device 130. Computing device 130 may be a processor or a device that includes a processor, such as a laptop computer.

Figure 2:
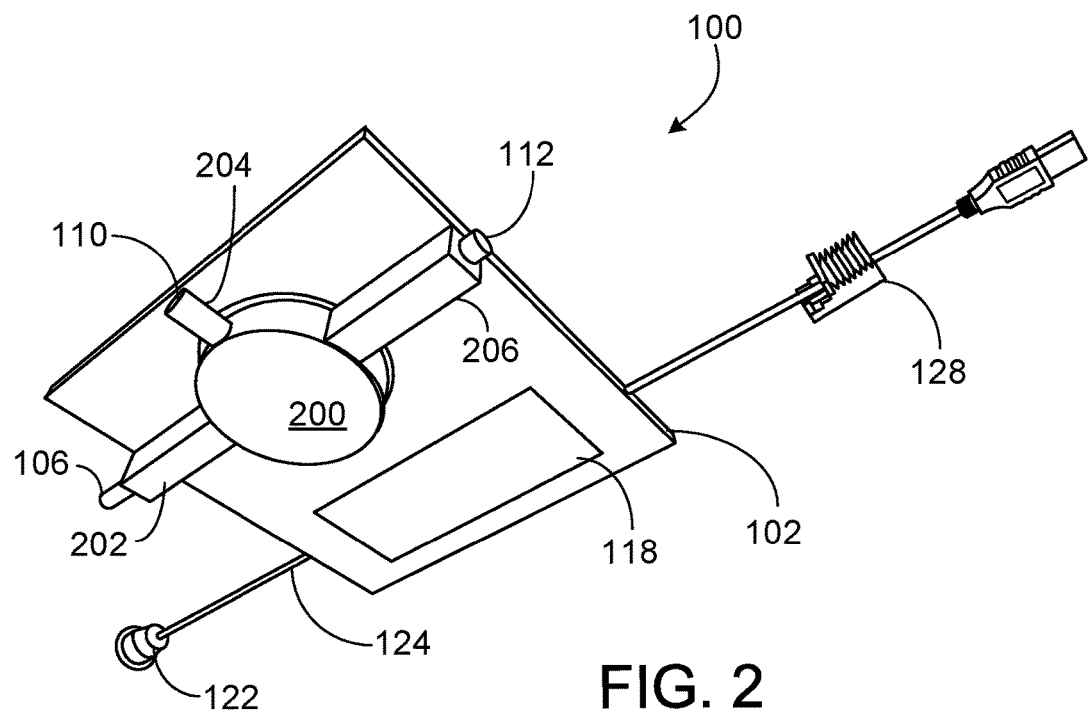
FIG. 2 is a perspective bottom view of the microfluidic device of FIG. 1.

FIG. 2 is a perspective view of a bottom of microfluidic device 100. As depicted in FIG. 2, bottom portion 200 of degassing chamber 108 is fluidly coupled to sample inlet 106 via conduit 202, to gas inlet 110 via conduit 204, and to waste outlet 112 via conduit 206. In one example, microfluidic device 100 has dimensions of 2 cm×2 cm×2 cm. Microfluidic device 100 may include pumps, valves, and other appropriate features to facilitate fluid flow through the device. In some embodiments, microfluidic device 100 includes a battery and is battery powered.

Operation of microfluidic device 100 is described with respect to FIGS. 1 and 2. An aqueous sample is provided to microfluidic device 100 via sample inlet 106. From sample inlet 106, the aqueous sample flows to bottom portion 200 of degassing chamber 108 via conduit 202. Gas (e.g., air or an inert gas such as nitrogen or helium), is provided to microfluidic device 100 via gas inlet 110 and flows to bottom portion 200 of degassing chamber 108 via conduit 204. Gas entering bottom portion 200 of degassing chamber 108 via conduit 204 strips gas (e.g., chlorine) from the aqueous sample into the gas phase. In some embodiments, a slight positive incoming pressure (e.g., less than about 5 psi) can be used to degas or to facilitate degassing of the aqueous sample. Gas, including gas stripped from the aqueous sample and gas provided to bottom portion 200 of degassing chamber 108 via conduit 204, as well as water vapor, passes through membrane 114 to upper portion 116 of degassing chamber 108. The portion of the aqueous sample remaining in bottom portion 200 of degassing chamber 108 exits microfluidic device 100 through waste outlet 112 via conduit 206. Gas in upper portion 116 of degassing chamber 108, including chlorine gas if present in the aqueous sample, flows to detection chamber 118 via conduit 120. In some embodiments, microfluidic device 100 operates in a continuous mode, with the aqueous sample flowing continuously into bottom portion 200 of degassing chamber 108 and gas stripped from the aqueous sample flowing continuously into detection chamber 118. Gas flowing to detection chamber 118 may be continuously monitored, or monitored at selected intervals.

Chlorine gas present in the aqueous sample is detected and quantified in detection chamber 118. Radiation from light source 122 is provided to detection chamber 118 via conduit 124, and gas molecules in the detection chamber absorb the radiation at known wavelengths. Chlorine gas ($Cl_2$) has a maximum light absorbance at 325 nm with a molar absorptivity of 70 $M^{-1}$ $cm^{-1}$. Other oxidant gases may also be detected at different wavelengths. Bromine gas ($Br_2$) has a maximum light absorbance at 390 nm with a molar absorptivity of 177 $M^{-1}$ $cm^{-1}$. $NH_2Cl$ can be detected at much shorter wavelengths (245 nm with a molar absorbance of 455 $M^{-1}$ $cm^{-1}$), and does not interfere with chlorine detection. Microfluidic device 100 may also be adapted to detect other gases by modifying the wavelength being monitored, the material properties of membrane 114, or both.

In detector 126, a ruled optical grating disperses the light in detection chamber 118 and focuses the light onto a CCD detector array. The CCD detector array quantifies the amount of light absorbed by chlorine gas in detection chamber 118. The quantity of light absorbed by the chlorine gas (Beer-Lambert's absorption law) is related to the number of chlorine molecules in the light path. Chlorine and other gas molecules have known absorption spectra and fingerprints, and are recognized by the CCD detector array. As such, multiple different gases in the light path all may be detected at the same time. Data from the CCD detector array are provided to data acquisition system 128 and relayed to computing device 130.

Only a few implementations are described and illustrated. Variations, enhancements and improvements of the described implementations and other implementations can be made based on what is described and illustrated in this document.

What is claimed is:
1. A microfluidic device comprising:
   a degassing chamber in the shape of a tube, the degassing chamber comprising a gas-permeable membrane and defining a first portion and a second portion of the degassing chamber along a length of the tube, wherein the first portion and the second portion are separated by the gas permeable membrane;

a sample inlet and a gas inlet fluidly coupled to the first portion of the degassing chamber through a circumferential wall of the degassing chamber and disposed at a right angle with respect to each other;

a light source;

a detection chamber fluidly coupled to the second portion of the degassing chamber; and a detector, wherein the light source and the detector are operably coupled to the detection chamber.

2. The microfluidic device of claim 1, further comprising a gas inlet fluidly coupled to the first portion of the degassing chamber.

3. The microfluidic device of claim 1, wherein the light source comprises a light-emitting diode.

4. The microfluidic device of claim 1, wherein the detector comprises a differential optical absorption spectrometer.

5. The microfluidic device of claim 1, wherein the detector comprises a charge-coupled device detector array.

6. The microfluidic device of claim 1, further comprising a battery operatively coupled to the detector.

7. The microfluidic device of claim 1, further comprising a data acquisition system operably coupled to the detector.

8. The microfluidic device of claim 1, further comprising a computing device operably coupled to the data acquisition system.

9. A microfluidic system comprising:

a microfluidic device comprising:

a degassing chamber in the shape of a tube, the degassing chamber comprising a gas-permeable membrane and defining a first portion and a second portion of the degassing chamber along a length of the tube, wherein the first portion and the second portion are separated by the gas permeable membrane;

a sample inlet and a gas inlet fluidly coupled to the first portion of the degassing chamber through a circumferential wall of the degassing chamber and disposed at a right angle with respect to each other; and a detection chamber fluidly coupled to the second portion of the degassing chamber, wherein detection chamber is fluidly coupled to the second portion of the degassing chamber.

10. The microfluidic system of claim 9, further comprising a light source operably coupled to the detection chamber.

11. The microfluidic system of claim 10, wherein the microfluidic device comprises the light source.

12. The microfluidic system of claim 10, wherein the light source is a light-emitting diode.

13. The microfluidic system of claim 9, further comprising a detector operably coupled to the detection chamber.

14. The microfluidic system of claim 13, further comprising one or more additional microfluidic devices, each comprising an additional detection chamber, wherein the detector is operably coupled to each additional detection chamber.

15. A method of assessing a concentration of chlorine gas in an aqueous sample, the method comprising:

providing an aqueous sample to the microfluidic device of claim 1;

separating gas from the aqueous sample in the microfluidic device;

providing the gas to the detector;

assessing the absorbance of the gas sample at a known absorption wavelength of chlorine; and based on the assessed absorbance of the gas sample at the known absorption wavelength of chlorine, assessing a concentration of chlorine gas in the aqueous sample.

16. The method of claim 15, wherein separating the gas from the aqueous sample comprises contacting the aqueous sample with a gas-permeable membrane.

17. The method of claim 15, wherein separating the gas from the aqueous sample comprises contacting a purge gas with the aqueous sample.

18. The method of claim 15, further comprising providing the aqueous sample to the microfluidic device continuously.

19. The method of claim 15, wherein the aqueous sample is fluidly separated from the detector.

20. The method of claim 15, wherein assessing the concentration of chlorine gas in the aqueous sample occurs without combining a chemical reagent with the aqueous sample.

* * * * *